US009821128B2

(12) United States Patent
Morrison (10) Patent No.: US 9,821,128 B2
(45) Date of Patent: *Nov. 21, 2017

(54) SYSTEM AND METHOD FOR MONITORING NEBULIZATION OF A MEDICAMENT (75) Inventor: Mark Steven Morrison, Basking Ridge, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 961 days.

This patent is subject to a terminal disclaimer.

(21) Appl. No.: 13/130,145

(22) PCT Filed: Nov. 21, 2009

(86) PCT No.: PCT/IB2009/055255
§ 371 (c)(1),
(2), (4) Date: May 19, 2011

(87) PCT Pub. No.: WO2010/067239
PCT Pub. Date: Jun. 17, 2010

(65) Prior Publication Data
US 2011/0226235 A1 Sep. 22, 2011

Related U.S. Application Data
(60) Provisional application No. 61/121,582, filed on Dec. 11, 2008.

(51) Int. Cl.
*A61M 15/00* (2006.01)
*B05B 12/08* (2006.01)

(52) U.S. Cl.
CPC ....... *A61M 15/0085* (2013.01); *B05B 12/081* (2013.01); *A61M 2205/3375* (2013.01)

(58) Field of Classification Search
CPC .... A61M 11/00; A61M 11/005; A61M 15/00; A61M 15/0005; A61M 15/001; A61M 15/0065; A61M 15/0068; A61M 15/008; A61M 15/0085; A61M 16/14; A61M 16/18; A61M 2205/3375; A61M 2206/10; B05B 17/00; B05B 17/06; B05B 17/0607; B05B 17/0615; B05B 17/0623; B05B 17/063; B05B 17/0638; B05B 17/0646
USPC .......................... 128/200.16, 200.14, 203.15
See application file for complete search history.

(56) References Cited

U.S. PATENT DOCUMENTS

| | | | | |
|---|---|---|---|---|
| 4,582,654 A * | 4/1986 | Karnicky et al. | ................ | 261/91 |
| 4,996,502 A * | 2/1991 | Endo | ................ | 331/46 |
| 5,452,711 A * | 9/1995 | Gault | ................ | 128/200.14 |
| 5,709,202 A * | 1/1998 | Lloyd et al. | ............ | 128/200.14 |
| 5,794,612 A * | 8/1998 | Wachter et al. | ......... | 128/200.23 |
| 6,152,130 A * | 11/2000 | Abrams et al. | .......... | 128/204.21 |

(Continued)

FOREIGN PATENT DOCUMENTS

GB 2013343 A * 8/1979

*Primary Examiner* — Michael Tsai
(74) *Attorney, Agent, or Firm* — Michael W. Haas (57) ABSTRACT

Nebulization of a medicament for delivery to a subject is monitored. In one embodiment, whether there is any medicament to be nebulized, a rate of nebulization, and/or other aspects of the nebulization of the medicament are monitored. Information related to the one or more monitored aspects of the nebulization may be provided to a subject. For example, by monitoring whether there is any medicament to be nebulized, whether the nebulization of the medicament is complete may be determined.

18 Claims, 4 Drawing Sheets

(56) References Cited

U.S. PATENT DOCUMENTS

| | | | |
|---|---|---|---|
| 6,357,671 B1* | 3/2002 | Cewers | 239/102.2 |
| 6,402,046 B1* | 6/2002 | Loser | 239/4 |
| 6,601,581 B1* | 8/2003 | Babaev | 128/200.16 |
| 6,889,690 B2* | 5/2005 | Crowder et al. | 128/203.15 |
| 2002/0156400 A1 | 10/2002 | Babaev | |
| 2003/0146300 A1* | 8/2003 | Denyer et al. | 239/338 |
| 2006/0091878 A1* | 5/2006 | Wilson et al. | 324/76.14 |
| 2006/0102172 A1* | 5/2006 | Feiner et al. | 128/200.14 |
| 2006/0249144 A1* | 11/2006 | DeHaan et al. | 128/200.14 |
| 2007/0215149 A1 | 9/2007 | King et al. | |
| 2007/0240712 A1* | 10/2007 | Fleming et al. | 128/203.15 |
| 2007/0277816 A1* | 12/2007 | Morrison et al. | 128/200.16 |
| 2008/0173729 A1* | 7/2008 | Weng et al. | 239/102.2 |

\* cited by examiner

FIG. 4

SYSTEM AND METHOD FOR MONITORING NEBULIZATION OF A MEDICAMENT

This patent application claims the priority benefit under 35 U.S.C. §119(e) of U.S. Provisional Application No. 61/121,582 filed on Dec. 11, 2008, the contents of which are herein incorporated by reference.

This application is related to U.S. Patent Application Ser. No. 61/121,580, entitled "SYSTEM AND METHOD FOR MONITORING A METERED DOSE INHALER," filed Dec. 11, 2008, which is hereby incorporated into this application in its entirety.

The invention relates to monitoring nebulization of a medicament based on ultrasonic energy emitted during the nebulization of the medicament.

Nebulizer systems that nebulize medicament for delivery to subjects are known. Generally, these systems do not monitor the nebulization of the medicament in a manner that is meaningful to the subject. As a non-limiting example, no indication may be given to the user of an end of a nebulization treatment (e.g., when all (or substantially all) of the medicament has been nebulized). As such, treatments may effectively be extended because the subject is not able to determine when use of the nebulizer can be stopped.

One aspect of the invention relates to a system configured to monitor one or more aspects of nebulization of a medicament. In one embodiment, the system comprises a sensor, and a processor. The sensor is configured to generate one or more output signals conveying information related to ultrasonic energy generated during nebulization of a medicament. The processor is configured to receive the one or more output signals generated by the sensor, and to monitor one or more aspects of the nebulization of the medicament based on the information related to the ultrasonic energy generated during the nebulization of the medicament that is conveyed by the received one or more output signals.

Another aspect of the invention relates to a method of monitoring one or more aspects of nebulization of a medicament. In one embodiment, the method comprises generating one or more output signals conveying information related to ultrasonic energy generated during nebulization of a medicament; monitoring one or more aspects of the nebulization of the medicament based on the generated one or more output signals; and providing information to a subject of the nebulization related to the monitored one or more aspects of the nebulization.

Yet another aspect of the invention relates to a system configured to monitor one or more aspects of nebulization of a medicament. In one embodiment, the system comprises means for generating one or more output signals conveying information related to ultrasonic energy generated during nebulization of a medicament; means for monitoring one or more aspects of the nebulization of the medicament based on the generated one or more output signals; and means for providing information to a subject of the nebulization related to the monitored one or more aspects of the nebulization.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
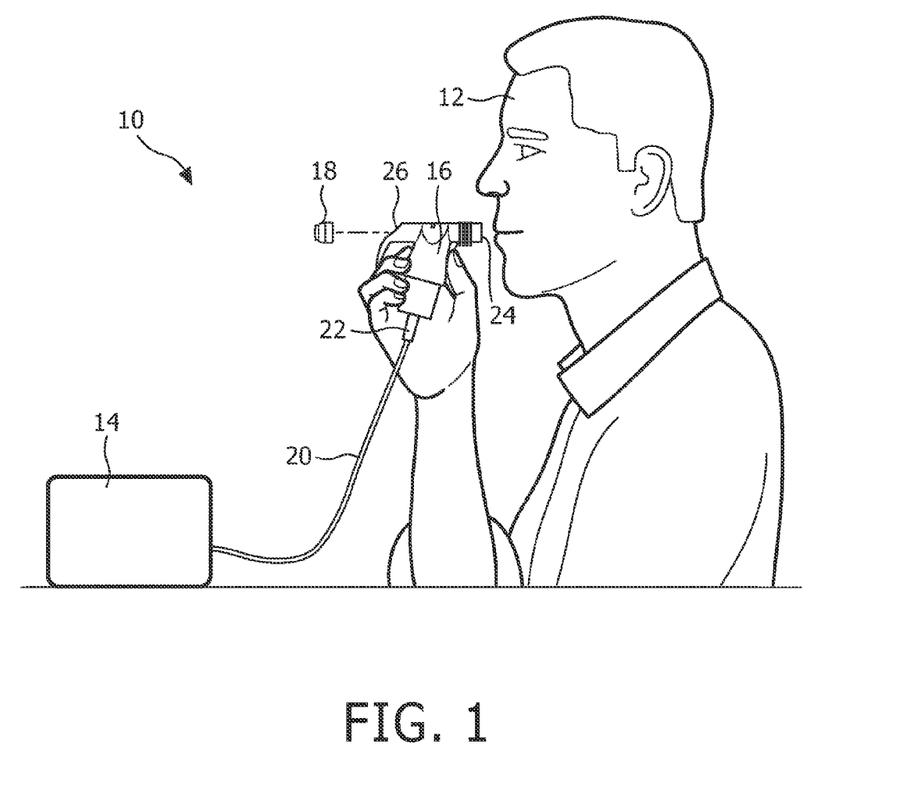
FIG. 1 illustrates a system configured to monitor nebulization of a medicament, in accordance with one or more embodiments of the invention.

FIG. 1 illustrates a system 10 configured to monitor the nebulization of a medicament for delivery to a subject 12, according to one embodiment of the invention. In one embodiment, system 10 may monitor whether there is any medicament to be nebulized, a rate of nebulization, one or more properties of the medicament being nebulized (e.g., viscosity, composition, etc.), and/or other aspects of the nebulization of the medicament. By monitoring whether there is any medicament to be nebulized, system 10 effectively monitors whether the nebulization of the medicament is complete. This may enhance the nebulization of the medicament at least in that subject 12 is provided with a reliable indication of when the nebulization is complete. Without this indication provided by system 10, subject 12 may be forced to rely on less reliable indicators of nebulization completion, which may unnecessarily prolong the time subject 12 receives treatment (e.g., if subject 12 continues to attempt nebulization after all of the medicament is gone). In one embodiment, system 10 comprises one or more of a pressurized gas source 14, a nebulizer handset 16, and/or a nebulization monitor 18.

Pressurized gas source 14 provides a pressurized flow of gas that nebulizes a medicament for delivery to subject 12. In one embodiment, pressurized gas source 14 includes one or more valves for controlling the release of the pressurized gas from pressurized gas source 14. By way of non-limiting example, pressurized gas source 14 may include one or more of a wall-gas source, a blower, a pressurized tank or canister of gas, a piston, a diaphragm, and/or other pressurized sources of gas.

Nebulizer handset 16 receives the flow of pressurized gas from pressurized gas source 14 and implements the pressurized flow to nebulize a medicament for delivery to subject 12. In the embodiment shown in FIG. 1, nebulizer handset 16 communicates with pressurized gas source 14 (e.g., to receive pressurized gas) via a conduit 20 that runs therebetween. In some embodiments (not shown here), nebulizer handset 16 may be connected directly to pressurized gas source 14.

Nebulizer handset 16 includes a pressurized gas inlet 22, a medicament outlet 24, and an exhaust outlet 26. Nebulizer handset 16 further comprises a medicament reservoir that is not shown in FIG. 1 because it is formed within nebulizer handset 16. The medicament reservoir is adapted to hold one or more bodies of medicament to be nebulized therein. Pressurized gas is received from pressurized gas source 14 into nebulizer handset 16 at pressurized gas inlet 22. The pressurized gas is introduced to medicament held by nebulizer handset 16 (e.g., within medicament reservoir) in such a manner that the pressurized gas nebulizes the medicament. The nebulized medicament is then received by subject 12 through medicament outlet 24. In one embodiment, subject 12 engages medicament outlet 24 with his mouth, and inhales to receive the nebulized medicament from medicament outlet 24. Gas exhaled by subject 12 into medicament outlet 24 and/or pressurized gas received into nebulizer handset 16 via pressurized gas inlet 22 may be exhausted from nebulizer handset 16 via exhaust outlet 26. In some implementations, nebulizer handset 16 may include one or more mechanisms to prevent medicament from being exhausted through exhaust outlet 26. These one or more mechanisms may include, for example, one or more baffles or valves disposed within nebulizer handset 16 and/or at or near exhaust outlet 26.

During operation, pressurized gas source 14 and/or pressurized gas provided by pressurized gas source 14 through conduit 20 and nebulizer handset 16 may generate audible white noise. This white noise includes noise generated by the actual nebulization of medicament within nebulizer handset 16. The tone of the white noise generated by the actual nebulization of medicament may vary somewhat with the level of the medicament in the medicament reservoir within nebulizer handset 16, and/or with other aspects of the nebulization of the medicament. However, changes in the tone of the white noise generated by actual nebulization of medicament may be relatively small and/or may be drowned out by the other sources of white noise during nebulization (e.g., a motor of pressurized gas source 14, gas rushing through a valve at pressurized gas source 14, gas traveling through conduit 20, gas moving from conduit 20 to nebulizer handset 16, etc.). As such, subject 12 may have difficulty detecting sputtering, which occurs as the medicament begins to run out, an end of nebulization due to an absence of medicament, and/or information related to other aspects of the nebulization based solely on the sounds produced by system 10 during nebulization. Further, other ambient noise, hearing loss, and/or other factors may contribute to the difficulty of such a detection.

Nebulization monitor 18 is configured to monitor one or more aspects of the nebulization of the medicament within nebulizer handset 16, and to provide information to subject 12 related to the monitored one or more aspects. For example, nebulization monitor 18 may monitor whether the nebulization of medicament within nebulization head 16 is causing sputtering, whether there is any medicament left in the medicament reservoir of nebulizer handset 16, and/or other aspects of the nebulization of the medicament within nebulization head. Nebulization monitor 18 monitors the one or more aspects of the nebulization based on ultrasonic energy generated by system 10 during nebulization.

In one embodiment (not shown here), nebulization monitor 18 is formed integrally with nebulizer handset 16 such that nebulization monitor 18 is not designed to be removed and used with another nebulizer handset. In one embodiment, nebulization monitor 18 is selectably removable from a nebulization head of nebulizer handset 16, the removable nebulization monitor 18 may be designed to be usable with a plurality of different nebulization heads. Further, although nebulization monitor 18 is illustrated in FIG. 1 as being wholly carried on nebulizer handset 16, this is not intended to be limiting. In one embodiment, some of all of the components of nebulization monitor 18 may be entirely separate from nebulizer handset 16. For example, some or all of the components of nebulization monitor 18 may be carried on pressurized gas source 14, conduit 20, and/or may be separate and unattached from all of the other components of system 10.

Figure 2:
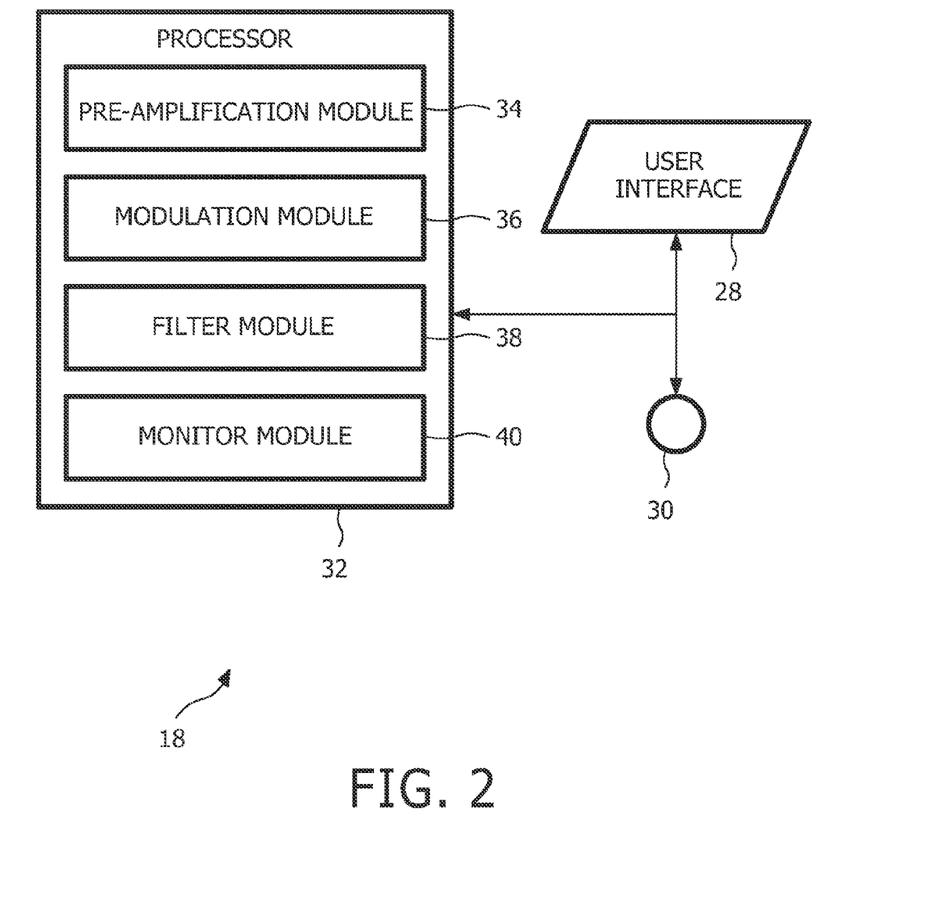
FIG. 2 illustrates a nebulization monitor, according to one or more embodiments of the invention.

FIG. 2 illustrates a functional block diagram of nebulization monitor 18, in accordance with one embodiment of the invention. In the embodiment illustrated in FIG. 2, nebulization monitor 18 includes a user interface 28, a sensor 30, and a processor 32. It should be appreciated that this is for illustrative purposes only, as nebulization monitor 18 may, in some embodiments, include more or less components than are illustrated in the block diagram of FIG. 2.

User interface 28 is configured to provide an interface between nebulization monitor 18 and subject 12 through which subject 12 may receive information from nebulization monitor 18. This enables data, results, and/or instructions and any other communicable items, collectively referred to as "information," to be communicated between the subject 12 and the other components of nebulization monitor 18. In one embodiment, the form factor of nebulization monitor 18 is a consideration in the design of user interface 28. In this embodiment, the interface provided by user interface 28 may be relatively small and/or uncomplicated to limit the space that it takes up. Examples of interface devices suitable for inclusion in user interface 28 include a display screen, speakers, one or more indicator lights, an audible alarm, and/or other interface devices.

Sensor 30 is configured to generate one or more output signals conveying information related to ultrasonic energy generated during nebulization of a medicament (e.g., within nebulizer handset 16 shown in FIG. 1 and described above). As such, sensor 30 may include a transducer configured to convert ultrasonic energy to an electronic output signal (e.g., a current, a voltage, etc.). In one embodiment, sensor 30 includes an ultrasonic microphone (e.g., a microphone sensitive to frequencies higher than audible frequencies), a piezoelectric transducer, and/or other transducers capable of converting ultrasonic energy to an electronic output signal.

Ultrasonic energy generated by the operation of a nebulizer (e.g., pressurized gas source 14, nebulizer handset 16, and conduit 20 shown in FIG. 1 and described above) is typically modulated at a lower frequency (e.g., within the audible range) in a manner that is impacted by whether the operation of the nebulizer is actually nebulizing medicament, the rate at which medicament is being nebulized, one or more properties of the medicament (e.g., viscosity, composition, etc.), and/or other aspects of the nebulization of medicament by the nebulizer. For example, in one embodiment, the ultra sonic energy generated by the nebulizer is modulated at one or more frequencies in the audible range while medicament is actually being nebulized, but this modulation decreases in amplitude and/or disappears altogether if the nebulizer is still being operated and no medicament is being nebulized (e.g., due to an empty reservoir in the nebulizer). As such, in one embodiment, the information related to ultrasonic energy generated during nebulization that is conveyed by the one or more output signals generated by sensor 30 enables detection of an ultrasonic carrier wave that carries a modulated signal indicating whether the operation of the nebulizer is actually nebulizing medicament, a rate at which medicament is being nebulized by the nebulizer, one or more properties of the medicament (e.g., viscosity, composition, etc.), and/or other aspects of the nebulization.

Processor 32 is configured to provide information processing capabilities in nebulization monitor 18. As such, processor 32 may include one or more of a digital processor, an analog processor, a digital circuit designed to process information, an analog circuit designed to process information, a state machine, and/or other mechanisms for electronically processing information. Although processor 32 is shown in FIG. 2 as a single entity, this is for illustrative purposes only. In some implementations, processor 32 may include a plurality of processing units. These processing units may be physically located within the same device, or processor 32 may represent processing functionality of a plurality of devices operating in coordination.

As is shown in FIG. 2, in one embodiment, processor 32 includes a pre-amplification module 34, a modulation module 36, a filter module 38, a monitor module 40, and/or other modules. Modules 34, 36, 38, and/or 40 may be implemented in software; hardware; firmware; some combination of software, hardware, and/or firmware; and/or otherwise implemented. It should be appreciated that although modules 34, 36, 38, and/or 40 are illustrated in FIG. 2 as being co-located within a single processing unit, in implementations in which processor 32 includes multiple processing units, modules 34, 36, 38, and/or 40 may be located remotely from the other modules. Further, the description of the functionality of modules 34, 36, 38, and/or 40 provided below is for illustrative purposes, and is not intended to be limiting, as any of modules 34, 36, 38, and/or 40 may provide more or less functionality than is described. For example, one or more of modules 34, 36, 38, and/or 40 may be eliminated, and some or all of its functionality may be provided by other ones of modules 34, 36, 38, and/or 40. As another example, processor 32 may include one or more additional modules that perform some or all of the functionality attributed below to one of modules 34, 36, 38, and/or 40.

Pre-amplification module 34 is configured to amplify the one or more output signals generated by sensor 30. In one embodiment, pre-amplification module 34 pre-amplifies the one or more output signals prior to subsequent processing by the modules of processor 32. The pre-amplification of the one or more output signals may facilitate the subsequent processing.

Figure 3:
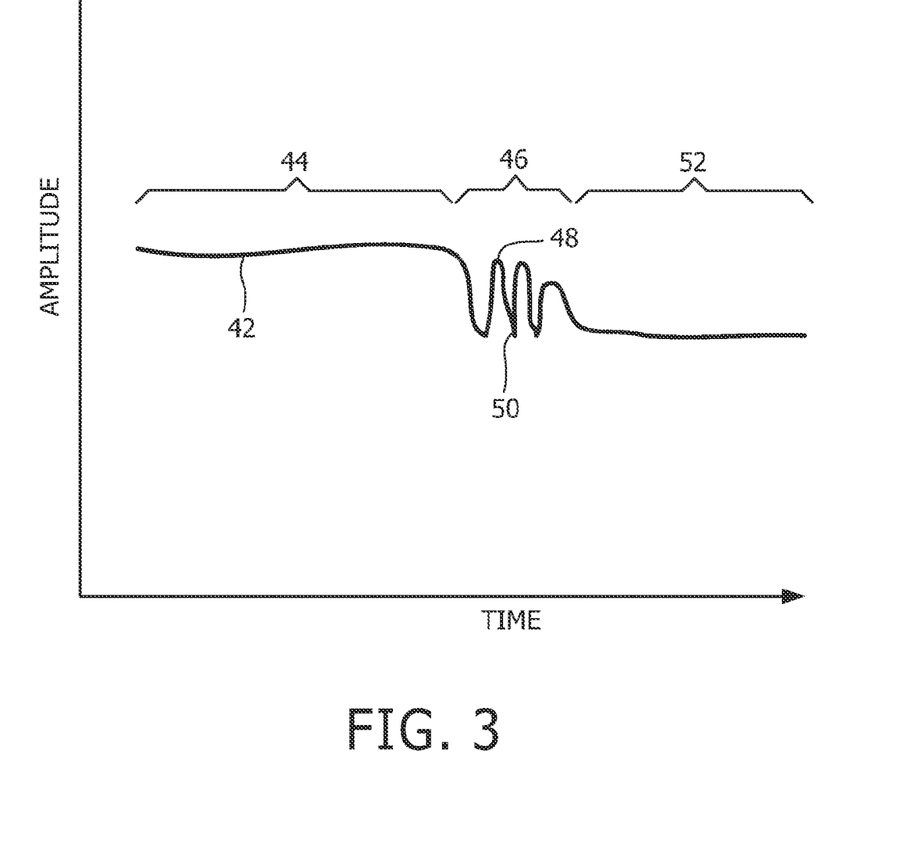
FIG. 3 illustrates a plot of a signal through which ultrasonic energy generated during the operation of a nebulizer can be monitored, in accordance with one or more embodiments of the invention.

Modulation module 36 is configured to extract a modulated signal that is carried by an ultrasonic carrier signal detected from one or more of the output signals generated by sensor 30. In one embodiment, the modulated signal may include one or more signals within a sub-sonic frequency. In one embodiment, the modulated signal may include one or more signals within the audible range that convey information about one or more aspects of nebulization of a medicament. For example, the modulated signal may include a signal between about 1 kHz and about 10 kHz. In one embodiment, modulation module 36 comprises a rectifier that extracts the modulated signal from the ultrasonic carrier signal present in the one or more output signals generated by sensor 30.

Filter module 38 is configured to filter the modulated signal that is extracted by modulation module 36. In some instances, in addition to signals that convey information about nebulization of a medicament, the modulated signal may include noise and/or signals at frequencies that are not of interest. Filter module 38 may filter out frequencies of the modulated signal that interfere with the signal(s) that convey information about nebulization of a medicament. For example, in one embodiment, filter module 38 includes a band-pass filter with a range that includes at least some audible frequencies. The range of the band-pass filter may be, for instance, between about 2 kHz and about 10 kHz.

Monitor module 40 is configured to monitor nebulization of a medicament based on the filtered signal provided by filter module 38. As should be apparent from the foregoing, the filtered signal, which was originally carried in the ultrasonic energy generated by operation of a nebulizer, conveys information related to whether medicament is being nebulized, a rate at which medicament is being nebulized, and/or other aspects of the nebulization. Monitor module 40 receives the filtered signal from filter module 38, and determines information related to one or more aspects of the nebulization of the medicament by the nebulizer from the filtered signal. The signal received by monitor module 40 is not subject to white noise generated through operation of the nebulizer and/or white noise present in the environment. This is because the signal received by monitor module 40 was originally carried in the ultrasonic energy generated by the nebulization of the medicament, whereas the sources of white noise are merely carried in sound waves surrounding the nebulizer and are not present in the ultrasonic energy emanating from the nebulization of the medicament. In one embodiment, monitor module 40 includes a frequency to voltage converter that converts the frequency information included within the filtered signal received from filter module 38 into voltage information. The voltage information is then monitored to determine information related to one or more aspects of the nebulization of the medicament by the nebulizer. In one embodiment, information related to the one or more aspects of the nebulization of the medicament determined by monitor module 40 are conveyed to a user via user interface 28.

FIG. 3 illustrates a plot of a signal 42 monitored by one embodiment of a monitor module similar to or the same as monitor module 40 (shown in FIG. 2 and described above) to determine information related to the nebulization of a medicament. In particular, the plot shown in FIG. 3 represents a frequency-to-voltage conversion performed by the monitor module. As was mentioned above, the ultrasonic energy generated during operation of a nebulizer is modulated with a signal that varies in response to changes in one or more aspects of the operation of a signal modulated onto the ultrasonic energy as a function of time. During a first time period 44, the presence of the modulated signal carried by the ultrasonic energy, represented by an elevated amplitude in signal 42, indicates that the operation of the nebulizer is actually nebulizing a medicament. As such, during first time period 44, medicament is present in the medicament reservoir of the nebulizer, and is available for nebulization. During a second time period 46, the vacillation in the amplitude of the signal 42 indicates at points in time (e.g., point 48) the operation of the nebulizer is nebulizing medicament, while at other points in time (e.g., point 50) the operation of nebulizer is not nebulizing medicament. This sporadic nebulization of medicament is commonly referred to as "sputtering," and indicates that the level of medicament present within the reservoir of the nebulizer is reaching a level at which nebulization will no longer take place (e.g., it will become empty). At a third period of time 52, the persistent depression of the amplitude of signal 42 indicates that the modulated signal is not present in the ultrasonic energy emanating from the nebulizer because the operation of the nebulizer is not nebulizing medicament. This is most commonly associated with the medicament reservoir of the nebulizer being empty.

Returning to FIG. 2, in one embodiment, monitor module 40 determines whether the operation of the nebulizer being monitored by nebulization monitor 18 is nebulizing medicament from the signal received from filter module 38 in accordance with the principles discussed above with respect to FIG. 3. For example, in this embodiment, monitor module 40 may include a comparator that monitors a frequency-to-voltage conversion of the filtered signal that is provided to monitor module 40 by filter module 38 (e.g., a signal similar to signal 42 shown in FIG. 3). As was set forth above, the amplitude of this signal indicates whether medicament is being nebulized by the nebulizer or whether medicament is not being nebulized even if the nebulizer is being operated. Information about the nebulization of medicament determined by monitor module 40 from the filtered signal received from filter module 38 may be provided to the user via user interface 28, and the user can infer whether treatment is being received from the nebulizer, whether the operation of the nebulizer is resulting in sputter, and/or whether all (or substantially all) of the medicament has been nebulized from the user interface 28, thereby enabling the user to end the treatment in a timely manner.

It should be appreciated that the description of monitoring nebulization in a particular type of nebulizer (e.g., a jet nebulizer, a pneumatic nebulizer, etc.) is not intended to be limiting. The principles set forth above with respect to the monitoring of jet nebulizers will be readily applicable to other types of nebulizers for one of ordinary skill in the art without undue experimentation. Further, although the monitoring of a nebulization based on emitted ultrasonic energy has been described primarily for monitoring whether or not a nebulization treatment has been completed (e.g., there is no medicament left in the nebulizer), this is not limiting. Other aspects of nebulization may be monitored based on emitted ultrasonic energy in accordance with the principles described herein.

Figure 4:
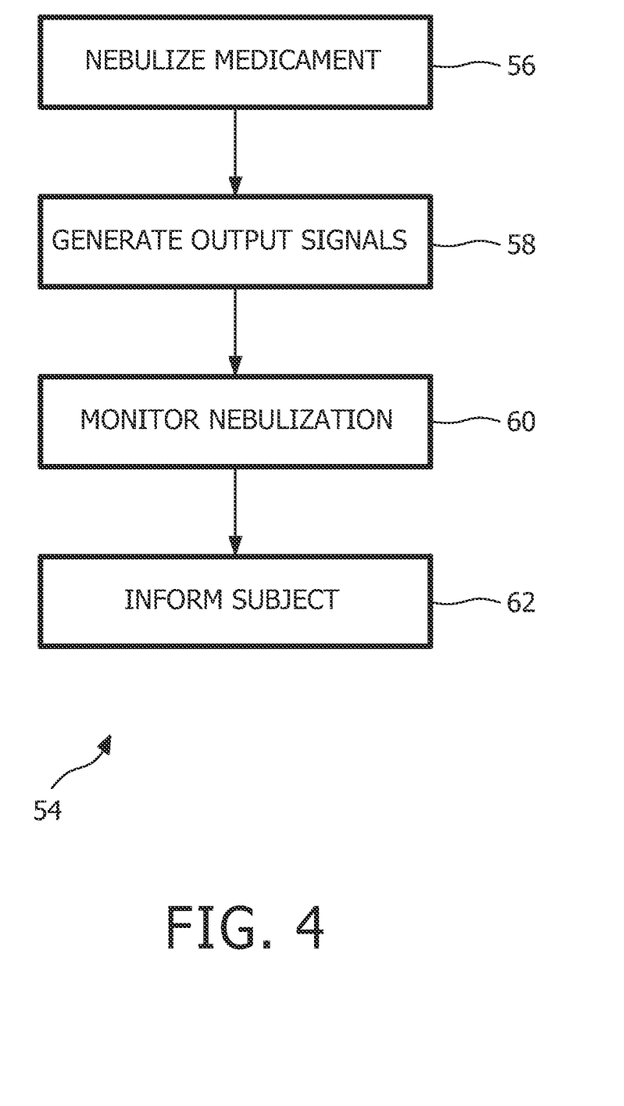
FIG. 4 illustrates a method of monitoring nebulization of a medicament, in accordance with one or more embodiments of the invention.

FIG. 4 illustrates a method 54 of monitoring one or more aspects of nebulization of a medicament. The operations of method 54 presented below are intended to be illustrative. In some embodiments, method 54 may be accomplished with one or more additional operations not described, and/or without one or more of the operations discussed. Additionally, the order in which the operations of method 54 are illustrated in FIG. 4 and described below is not intended to be limiting. Although the implementation of method 54 are described within the context of the systems set forth above, in some embodiments, method 54 is implemented in one or more other contexts.

Method 54 includes an operation 56, at which a medicament is nebulized for delivery to a patient. Operation 56 is performed by a nebulizer. For example, in one embodiment, the nebulizer may include a pressurized gas source, a conduit, and a nebulizer handset that are the same as or similar to pressurized gas source 14, conduit 20, and nebulizer handset 16 (shown in FIG. 1 and described above), respectively.

At an operation 58, one or more output signals are generated that convey information related to ultrasonic energy generated during the nebulization of the medicament. In one embodiment, operation 58 is performed by a sensor that is the same as or similar to sensor 30 (shown in FIG. 2 and described above).

At an operation 60, one or more aspects of the nebulization of the medicament are monitored based on the generated one or more output signals. In one embodiment, operation 60 is performed by a processor that is the same as or similar to processor 32 (shown in FIG. 2 and described above).

At an operation 62, information related to the monitored one or more aspects of the nebulization are provided to a subject of the nebulization. In one embodiment, operation 62 is performed by a user interface that is the same as or similar to user interface 28 (shown in FIG. 2 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to monitor nebulization of medicament, the system comprising:
    an ultrasonic microphone configured to generate one or more output signals conveying information related to ultrasonic energy generated by nebulization of a medicament, wherein the ultrasonic energy generated by the nebulization of the medicament generates one or more output signals conveying an ultrasonic carrier signal modulated at a modulation frequency; and
    a processor configured to receive the one or more output signals generated by the ultrasonic microphone and extract a modulated signal from the ultrasonic carrier signal, and to monitor one or more aspects of the nebulization of the medicament based on the information that is conveyed by the received one or more output signals, wherein the processor is further configured to monitor the one or more aspects of the nebulization of the medicament based on the modulated signal.

2. The system of claim 1, wherein the modulation frequency is between about 1 kHz and about 10 kHz.

3. The system of claim 1, wherein the processor is configured to detect sputtering by monitoring an amplitude of the modulated signal.

4. The system of claim 1, wherein the processor is configured to monitor the one or more aspects of the nebulization of the medicament by determining whether a portion of the medicament remains to be nebulized.

5. The system of claim 1, further comprising a nebulizer configured to nebulize the medicament, wherein the ultrasonic energy is generated by the nebulizer.

6. The system of claim 1, further comprising a nebulizer handset carrying the ultrasonic microphone.

7. The system of claim 6, wherein the nebulizer handset further carries the processor.

8. The system of claim 1, further comprising a user interface that provides information to a subject related to the one or more aspects of the nebulization.

9. A method of monitoring nebulization of medicament, the method comprising:
    generating, by an ultrasonic microphone, one or more output signals conveying information related to ultrasonic energy generated by nebulization of a medicament wherein the ultrasonic energy generated by nebulization of the medicament generates one or more output signals conveying an ultrasonic carrier signal modulated at a modulation frequency;
    extracting a modulated signal from the ultrasonic carrier signal;
    monitoring one or more aspects of the nebulization of the medicament based on the one or more output signals, wherein monitoring the one or more aspects of the nebulization of the medicament is further based on the modulated signal; and
    obtaining information related to the one or more aspects of the nebulization.

10. The method of claim 9, wherein the modulation frequency is between about 1 kHz and about 10 kHz.

11. The method of claim 9, further comprising:
detecting sputtering by monitoring an amplitude of the modulated signal.

12. The method of claim 9, wherein monitoring the one or more aspects of the nebulization of the medicament comprises monitoring whether a portion of the medicament remains to be nebulized.

13. The method of claim 9, further comprising nebulizing, by a nebulizer, the medicament, wherein the ultrasonic energy is generated by the nebulizer.

14. A system configured to monitor nebulization of medicament, the system comprising:

an ultrasonic microphone configured to generate one or more output signals conveying information related to ultrasonic energy generated by nebulization of a medicament, wherein the ultrasonic energy generated by nebulization of the medicament generates one or more output signals conveying an ultrasonic carrier signal modulated at a modulation frequency;

means for extracting a modulated signal from the ultrasonic carrier signal;

means for monitoring one or more aspects of the nebulization of the medicament based on the one or more output signals, wherein operation by the means for monitoring is further based on the modulated signal; and means for providing information related to the one or more aspects of the nebulization.

15. The system of claim 14, wherein the modulation frequency is between about 1 kHz and about 10 kHz.

16. The system of claim 14, wherein operation of the means for monitoring includes means for detecting sputtering by monitoring an amplitude of the modulated signal.

17. The system of claim 14, wherein the means for monitoring the one or more aspects of the nebulization of the medicament comprises means for monitoring whether a portion of the medicament remains to be nebulized.

18. The system of claim 14, further comprising means for nebulizing the medicament, wherein the ultrasonic energy is generated by the means for nebulizing.

* * * * *